United States Patent
Rinaldi et al.

(10) Patent No.: US 6,379,740 B1
(45) Date of Patent: Apr. 30, 2002

(54) METHOD FOR TREATING A PROSTHESIS HAVING AN APERTURED STRUCTURE AND ASSOCIATED DEVICES

(75) Inventors: Stefano Rinaldi, Parma; Arnaldo Giannetti, Vercelli; Enrico Pasquino, Turin, all of (IT)

(73) Assignee: Sorin Biomedica Cardio S.p.A., Saluggia (IT)

( * ) Notice: Subject to any disclaimer, the term of this patent is extended or adjusted under 35 U.S.C. 154(b) by 0 days.

(21) Appl. No.: 09/209,433

(22) Filed: Dec. 10, 1998

(30) Foreign Application Priority Data

Dec. 10, 1997 (IT) .......................................... TO97A1068

(51) Int. Cl.⁷ ........................... A61L 27/00; B05D 7/22; B05D 1/18
(52) U.S. Cl. ......................... 427/2.1; 427/2.24; 427/2.3; 427/2.31; 427/238; 427/243; 427/244; 427/245; 427/294; 427/295; 427/296
(58) Field of Search ............................... 427/2.1, 2.24, 427/2.3, 2.31, 238, 243, 244, 245, 294, 295, 296

(56) References Cited

U.S. PATENT DOCUMENTS

| | | | |
|---|---|---|---|
| 4,976,736 A | * | 12/1990 | White et al. .................... 623/16 |
| 5,108,436 A | * | 4/1992 | Chu et al. ....................... 623/66 |
| 6,143,293 A | * | 11/2000 | Weiss et al. ................ 424/93.7 |
| 6,159,417 A | * | 12/2000 | Giordano .................... 264/628 |
| 6,210,715 B1 | * | 4/2001 | Starling et al. ............. 424/489 |

\* cited by examiner

*Primary Examiner*—Shrive P. Beck
*Assistant Examiner*—Jennifer Kolb Michener
(74) *Attorney, Agent, or Firm*—Popovich & Wiles, P.A.

(57) ABSTRACT

A prosthesis having an apertured structure is located in a chamber (11) which is taken to sub-atmospheric pressure. Once sub-atmospheric pressure has been reached, a liquid, optionally containing pharmacological agents, is introduced into the chamber. Drawn by the sub-atmospheric pressure, the liquid saturates the apertured structure of the prosthesis. In this way, the invention eliminates the risk of air being trapped in the apertured structure that could give rise to the formation of blood clots after implantation of the prosthesis. The liquid can contain drugs that penetrate the prosthesis, performing their therapeutic action locally and over time after implantation.

6 Claims, 3 Drawing Sheets

METHOD FOR TREATING A PROSTHESIS HAVING AN APERTURED STRUCTURE AND ASSOCIATED DEVICES

FIELD OF THE INVENTION

The present invention generally relates to a method for treating prostheses having an apertured structure. In particular, this invention relates to a method and a device for saturating a prosthesis with a liquid.

BACKGROUND OF THE INVENTION

The term "apertured structure" refers to those prostheses (such as, for example, so-called vascular grafts or the suture rings of cardiac valve prostheses) comprising, entirely or in part, from tissue structures, spongy masses and/or having elaborate geometries with slits, cavities and spaces, i.e., apertures. In use, such prostheses tend to hold air inside them with a consequent risk of the formation of blood clots in the period following implantation, due to the presence of air bubbles contained or otherwise held by the prosthesis. The simple solution, sometimes adopted during the implantation operation, of immersing the prosthesis in, for example, a physiological saline bath, does not satisfactorily solve the problem, both because the results can depend, possibly significantly, on the time dedicated to this treatment and the ability of the person conducting it, and because it is in any case difficult to remove all the air from the prosthesis.

SUMMARY OF THE INVENTION

The present invention therefore aims to eliminate in a radical manner the risk of the occurrence of these negative phenomena. The invention also concerns devices which can be used in the performance of this method. An important advantage of the invention is that the liquid such as, for example, physiological saline that is introduced into the pores, even the deep pores, to replace the air that is naturally present, can be supplemented with drugs such as, for example, antibiotics, anti-thrombotic drugs, drugs that promote the integration between the prosthesis and the surrounding biological tissues, or growth factors. Because the liquid is held in the pores, the drug or drugs can exert their action locally and extended over time. It is noted that the word "drug", as used herein, also includes the possible use of a binding agent applied to the prosthesis in order to attract thereto, with a binder-ligand association mechanism, pharmacologically active agents introduced into the patient's body.

In one aspect, this invention is a method for the treatment of a prosthesis having an apertured structure, comprising placing a prosthesis having an apertured structure into a holding chamber; producing sub-atmospheric pressure in the holding chamber; and introducing a liquid into the holding chamber to saturate the prosthesis. The sub-atmospheric pressure is selected so that after the introduction of the liquid into the holding chamber, the prosthesis is substantially free of air. The liquid may be substantially inert, e.g., physiological saline, or may comprise a drug. Sub-atmospheric pressure is established by connecting the holding chamber to a vacuum line, and liquid is introduced into the holding chamber by connecting the holding chamber to a liquid supply line, the liquid supply line being provided with a cut-off element. The sub-atmospheric pressure of the holding chamber reaches approximately −850 mbar. Preferably, the holding chamber is connected to the vacuum line for less than about 60 seconds and the liquid flows into the chamber for less than about 60 seconds.

In a second aspect, this invention is a device for the treatment of a prosthesis having an apertured structure comprising a casing defining a holding chamber for a prosthesis, the casing including an opening for the introduction of the prosthesis into the chamber and a sealing element disposed around the opening to allow a sub-atmospheric pressure to be drawn within the casing; a first fluid line leading to the casing for connecting the chamber to a source of sub-atmospheric pressure; a second fluid line for connecting the chamber to a source of liquid; and a valve acting on the first and second fluid lines to connect the chamber in succession with the source of sub-atmospheric pressure and the source of liquid. The source of liquid preferably is a container and a vacuum pump provides a source of sub-atmospheric pressure. Preferably, a safety cut-off element is interposed in the second fluid line, selectively activatable to open or close the second fluid line. Also, in a preferred embodiment, a filtration element comprising a sterile, fluid-permeable barrier is interposed in the first fluid line. A casing carrying a connector defines a common part of the first and second fluid lines. The connector may be a luer connector. The casing may have two complementary parts connectable together with the interposition of a sealing element; the two complementary parts may be sealingly connected together by locking means.

In a third aspect, this invention is a kit for the treatment of a prosthesis having an apertured structure, comprising a casing defining a holding chamber for a prosthesis, the casing including an opening for the introduction of the prosthesis into the chamber and a sealing element disposed around the opening to permit sub-atmospheric pressure to be drawn within the casing; a first fluid line leading to the casing for connecting the chamber to a source of sub-atmospheric pressure; a second fluid line for connecting the chamber to a source of liquid; and a valve acting on the first and second fluid lines to connect the chamber in succession with the source of sub-atmospheric pressure and the source of liquid, wherein the casing, the first fluid line, the second fluid line, and the valve are packaged in a sterile envelope.

In a fourth aspect, this invention is a container for a prosthesis having an apertured structure used to saturate the prosthesis with a liquid, the container comprising a casing defining a holding chamber for the prosthesis; at least one connector associated with the casing and configured to enable the connection of the prosthesis holding chamber to a source of sub-atmospheric pressure, the casing being sealably closable and having a structure that retains the substantial integrity of the prosthesis in the presence of sub-atmospheric pressure within the prosthesis holding chamber; and a liquid reservoir connected to the prosthesis holding chamber, such that the liquid from the reservoir saturates the apertured structure of the prosthesis as a result of the liquid being drawn into the holding chamber due to the sub-atmospheric pressure. The connector may be either a luer connector or a perforable membrane. Alternatively, the connector may be a luer connector integral with a perforable membrane.

BRIEF DESCRIPTION OF THE DRAWINGS

The invention will now be described, purely by way of non-limiting examples, with reference to the accompanying drawings, in which.

DETAILED DESCRIPTION OF THE PREFERRED EMBODIMENTS

Figure 1:
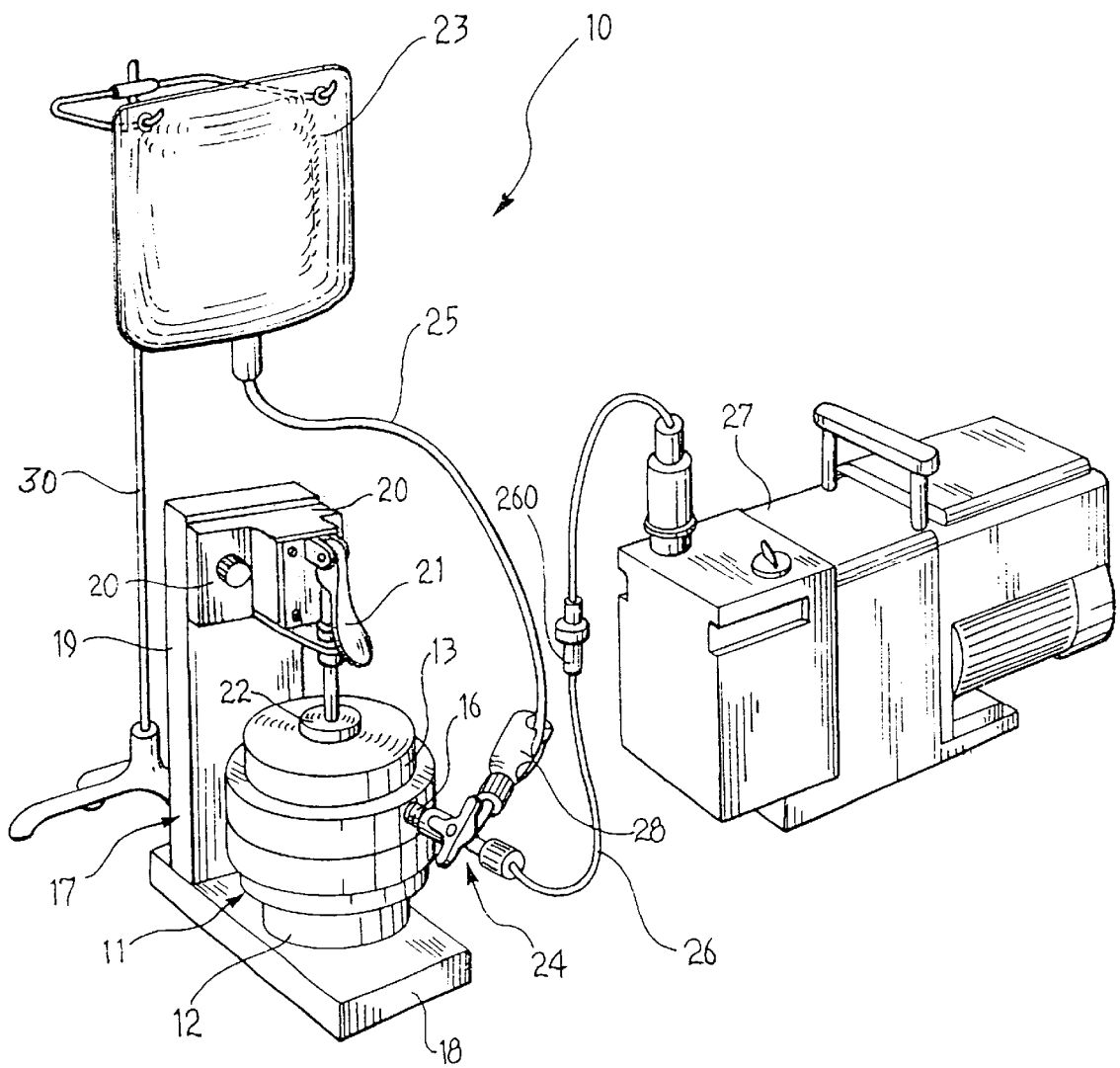
FIG. 1 shows a perspective view of a system for performing the method according to the invention.
Figure 3:
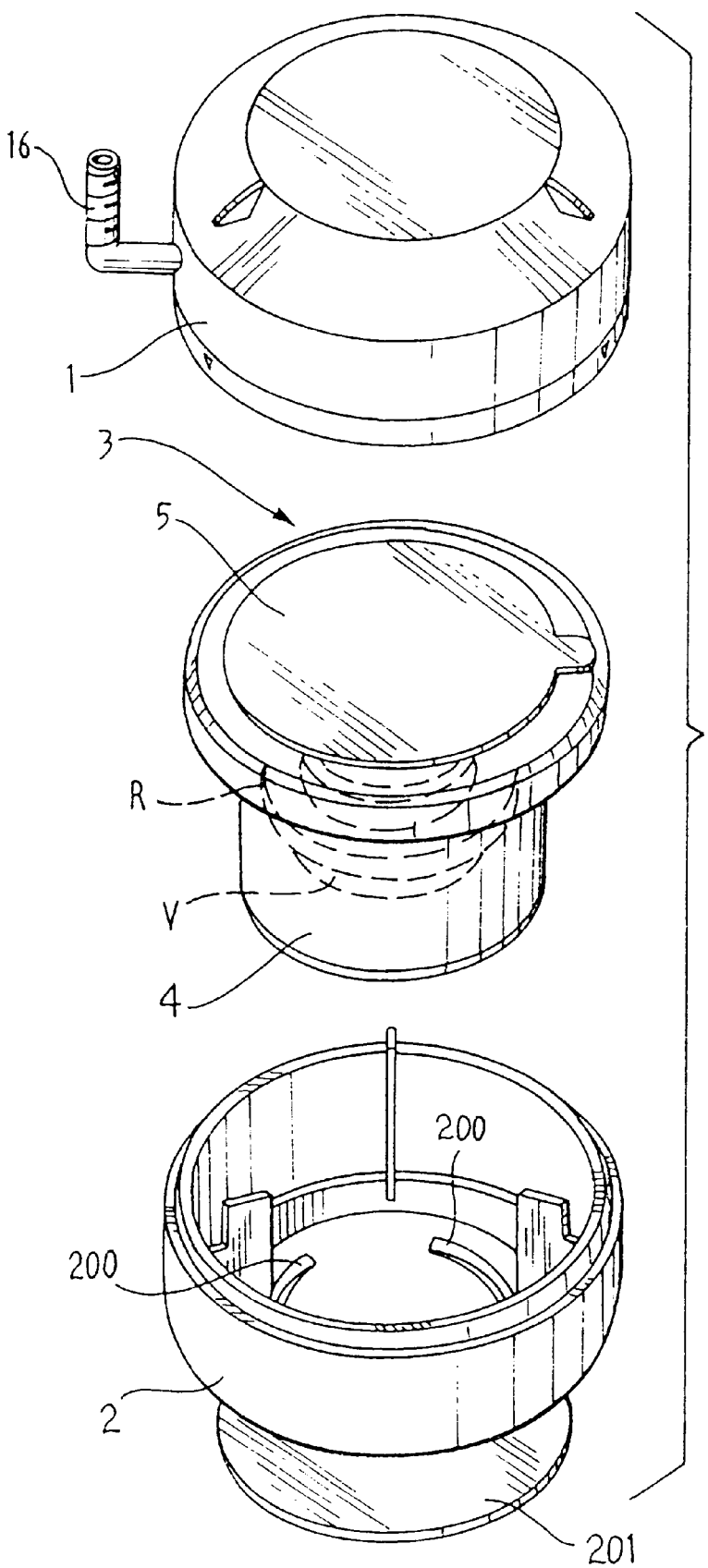
FIG. 3 illustrates a container for a prosthesis suitable for use in the invention.

Before proceeding to the description of FIG. 1, attention should be drawn to FIG. 3. This drawing illustrates a container that can be used for the sterile packaging of a prosthesis such as a cardiac valve prosthesis. With the exception of the presence of some characteristic elements (which will be referred to specifically below) relating to the application of the invention, the container illustrated in FIG. 3 corresponds to the container currently utilised by Sorin Biomedica Cardio S.p.A., Saluggia, Italy, for cardiac valve prostheses sold by Sorin Biomedica Cardio S.p.A. under the commercial name Bicarbon™. This container includes an outer shell formed from two cup-shape half shells 1 and 2 made from plastic material sealed (according to known criteria) along their respective mouth edges to define an inner chamber in which a further container 3 is located. Container 3 comprises cup-like body 4 within which the valve prosthesis V is located. Body 4 is closed along its mouth part by sealing disc 5. Sealing disc 5 is usually formed from a material able to form a sterile, although fluid-permeable, barrier. For example, it can be the material sold by DuPont, of Wilmington, Del. under the commercial name Tyvek®.

With the exception of the innovative elements referred to above, which will be described better below, the container of FIG. 3 is manufactured according to criteria that are widely known to one skilled in the art. This makes the description of further details superfluous as they are not in themselves necessary in order to understand and put into effect the invention.

Of course, the above also applies to the valve prosthesis V. In this case, it is sufficient to note that the valve prosthesis itself has a suture ring R of textile material, possibly with a spongy core, along its outer edge. In other words, it is a prosthesis having, at least in part, an "apertured" structure in the sense of the meaning described above.

The device illustrated in FIG. 1, generally indicated 10, includes a vacuum bell 11 as its main element. Vacuum bell 11 comprises a casing that is sealably closed or closable so that it can be taken to a desired level of sub-atmospheric pressure (i.e., to a "vacuum").

In the embodiment illustrated here (which is such that, as will be seen better below, the function of vacuum bell 11 can also be performed, for example, by the prosthesis container), bell 11 has the structure illustrated in greater detail in FIG. 2, being formed from cup-like holding body 12 with associated closure cover 13. Holding body 12 and cover 13 separate to form an opening. The dimensions and shape of cup-like body 12 are chosen so as to enable the prosthesis to be introduced into bell 11. In the embodiment illustrated here, the shape and dimensions of bell 11 are such that it can accommodate sterile container 3 holding the prosthesis, such as is shown in FIG. 3.

Both cup-like body 12 and cover 13 can be formed, for example, from a material such as a metal material or, even better, at least as regards cover 13, from a transparent plastic material such as polycarbonate or polymethacrylate so that it is possible to observe the inner chamber of bell 11 from the outside during the treatment which will be described below.

The method according to the invention is preferably performed in the operating theater, therefore in a sterile environment or close thereto. Consequently, the choice of materials forming the various parts of device 10 must take account of this preference and be sterilisable. Cover 13 comprises sealing element 14 disposed along its outer edge. The sealing element typically is a sealing gasket or ring (such as an O-ring). Cover 12 is traversed by radial duct 15 leading to one or more apertures opening into the upper part of the inner volume of bell 11 when cover 13 is fitted to body 12. Duct 15 leads to its outer end with respect to cover 13, and therefore to bell 11, at connector 16 (for example, of the type currently known as a "luer" connection) projecting outward from bell 11.

However, it is clear that the relative positioning of the parts described above is not in any way essential. For example, a sealing ring could be located on the mouth part of the cup-like body. The duct or ducts could have different paths and/or be provided on the cup-like body, or partly on the cup-like body and partly on the cover. Locking means such as clamp 17 enables bell 11 to be positioned and cover 13 to be held sealably closed on the mouth part of cup-like body 12 during the treatment of the prosthesis. In the embodiment illustrated here, clamp 17 includes base 18 defining a support surface for bell 11, pillar 19 extending vertically from the base 18, and an upper part 20 projecting over bell 11 positioned on base 18. Upper part 20 comprises toggle clamp element 21 of the type currently known as a Destaco clamp, leading to pressure foot 22.

Figure 2:
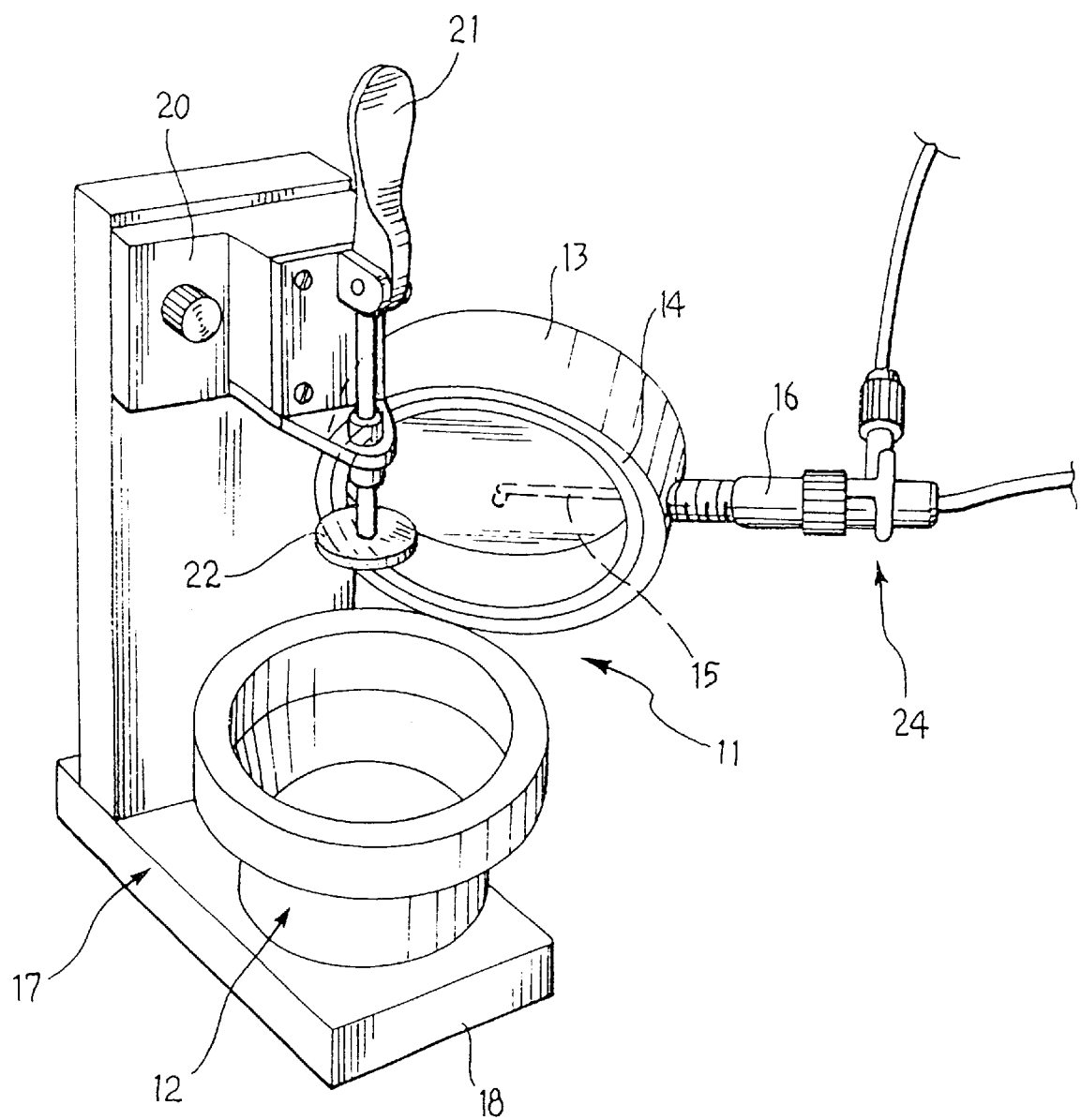
FIG. 2 illustrates in greater detail the structure of one of the parts shown in FIG. 1.

The method for positioning bell 11 in clamp 17 is clear from a comparison of FIG. 2 in which bell 11 is illustrated in an open position, with FIG. 1 in which bell 11, into which it is assumed that container 3 containing the prosthesis V has already been introduced, has been positioned in clamp 17. Toggle clamp 21 is then operated so that foot 22 presses cover 13 firmly against the mouth edge of cup-like body 12.

Container, reservoir, or bag 23 is a source of liquid and is located on associated pillar or support 30. Bag 23 contains a predetermined volume (for example, 200 cubic centimeters) of a liquid intended to be utilised for impregnating the apertured parts of the is prosthesis V according to the methods that will be better illustrated below. Preferably container or bag 23 is sterile. The liquid in question may be an inert liquid such as physiological saline, or an active liquid comprising one or more drugs. These drugs can also be added to the inert liquid in bag or container 23 through a suitable gate or opening using a technique well known in medical practice.

Valve 24 (such as a T-valve or other equivalent fluid handling component) is mounted on or otherwise connected to connector 16. Valve 24 permits the communication of connector 16 and thus duct 15 with fluid and vacuum lines. That is, as can be seen in FIG. 1, connector 16 communicates with vacuum line or first fluid line 26 that connects valve 24 to a source of sub-atmospheric pressure 27 (typically a vacuum pump or a vacuum line available wherever the treatment is effected, for example, in the operating theater). Connector 16 also communicates with second fluid line 25 that connects valve 24 to bag 23.

Fluid lines 25 and 26 can be formed, for example, from flexible tubing made from soft polyvinylchloride with an internal diameter of, for example, approximately 1 mm and an outer diameter of, for example, approximately 3.5 mm. Preferably, a cut-off element is interposed in fluid line 25, usually close to valve 24, which is able to interrupt line 25 if necessary. For example, safety cut-off switch or clamp 28 is shown interposed in line 25 to interrupt the flow of fluid from bag 23.

Filter 260 can be interposed at any point along the line 26 between the bell 11 and the source of sub-atmospheric pressure 27. The filter provides a sterile, fluid-permeable barrier. In the tests conducted by Sorin Biomedica Cardio S.p.A., a Leybold Trivac AF1.6 vacuum pump was used as the source of sub-atmospheric pressure.

With the possible application of the invention being directed towards the surgical field, this being preferable in many ways, the various parts of device 10 and, in particular, parts 12 and 13 of vacuum bell 11, together with the associated accessories (sealing gasket 14, bag 23, fluid lines 25 and 26, valve 24, etc.), preferably are formed from materials able to ensure the use of the method in a sterile environment. This therefore means that components are preferably formed as single use components and/or components that are sterilisable using, for example, ethylene oxide.

Preferably, the system for generating and applying the sub-atmospheric pressure (bell 11, pump 27 and associated connections, in the embodiment illustrated here) are chosen and dimensioned so as to ensure that a typical level of sub-atmospheric pressure of approximately −850 mbar is reached in the inner chamber of bell 11. Usually, system 10 is completed by a bath (not shown in the drawings) for collecting liquid from bag 23 that may be released on opening bell 11.

Preferably, the assembly formed by vacuum bell 11, valve 24, fluid lines 25 and 26, and, possibly, bag 23 is configured to be packaged in a sterile envelope, i.e., in the form of a kit. This arrangement enables the system to be used directly in the operating theater, and therefore at the time of implanting a prosthesis, such as the valve prosthesis V, in the following sequence of operations:

removing the equipment described above and connecting it via first fluid line 26 to the source of sub-atmospheric pressure 27, opening the outer container of the prosthesis by unrolling an adhesive strip (not shown) that connects the mouth parts of the half-shells 1 and 2 (it is recalled that the present description supposes that the prosthesis container corresponds to that illustrated in FIG. 3 without the further elements that will be described below), positioning inner container 3, in which the prosthesis V is located, into cup-like body 12 of bell 11, closing bell 11 with cover 13 and positioning bell 11 in clamp 17 which is then locked by acting on closure device 21, starting vacuum pump 27 (or, in any case, activating line 26 as the source of sub-atmospheric pressure), on reaching the required level of sub-atmospheric pressure (in the case of the level of −850 mbar and the kind of pump 27 referred to above, this result can be achieved quickly, typically, in less than about 60 seconds), switching valve 24 to the position that transfers connector 16, and thus duct 15, previously connected to line 26, to line 25, before opening safety clamp 28, if present. At this point, the liquid in bag 23 flows into the inner chamber of bell 11, penetrating the inside of container 3 (across seal 5 which is, as earlier noted, permeable). In this way, the liquid, possibly containing one or more drugs, completely saturates ring R, that is, the apertured part of the prosthesis, definitively preventing any air bubbles from being held therein or being able to enter it. If the liquid contains drugs, the drugs become trapped in the pores of the apertured part of the prosthesis and, consequently, can perform their pharmacological action locally over time following implantation;

deactivating vacuum pump 27 and, in any case, disconnecting valve 24 from the source of sub-atmospheric pressure;

completing the filling of the inner volume of bell 11 (which, in the conditions described above, can occur in a short period of time, this also being typically less than about 60 seconds) with the possible closure of safety clamp 28 and turning valve 24 to an emptying position;

opening clamp 17, with the consequent release therefrom of bell 11 which is opened to gain access to container 3; and releasing and opening container 3 by removing sealing layer 5 and extracting the prosthesis V, now ready for use.

Tests conducted by Sorin Biomedica Cardio S.p.A. show that this series of operations can be effected rapidly in surgery in not more than three minutes, including the time necessary to prepare device 10. In practice, the treatment described above, which leads to the complete removal of bubbles from the prosthesis (and its possible impregnation with drugs), can easily be achieved in a short time interval, thus making it completely compatible with the normal operation times.

The arrangement according to the invention is thus based on the principle of locating the prosthesis to be treated in a treatment chamber which is then taken to a level of sub-atmospheric pressure. This chamber is then connected to a liquid supply source (bag 23, in the embodiment illustrated) via a liquid supply line. Drawn by the sub-atmospheric pressure in the chamber (and possibly driven by an external over-pressurisation applied using known means, not specifically illustrated in the drawings: for example, squeezing bag 23, even manually can be sufficient), the liquid completely saturates the apertured parts of the prosthesis, preventing any air bubbles remaining or becoming trapped in the apertures. The liquid can be inert (such as, for example, physiological saline) or it can be a vehicle for active principals such as, for example, drugs. In this way, it is possible to obtain the additional result of saturating the apertured parts of the prosthesis with pharmacologically active principals that can be released gradually at the implantation site, effecting a local action over time. All of this has the further advantage that the nature and quantity of drug can be from time to time selected by the surgeon or surgeons depending on the specific implantation requirements, and this decision can be taken just moments before proceeding to implant the prosthesis.

The practical effectiveness of the arrangement described above has been tested by producing a device that enables the detection of any residual air trapped within the tissue meshes of the suture rings of valve prostheses currently produced by Sorin Biomedica Cardio S.p.A. The test device (not specifically illustrated in the drawings) enables a vacuum level to be achieved that corresponds to a pressure of not less than −20 mbar (therefore, a level close to the surface tension of water) on to beakers containing two suture rings immersed in an aqueous solution, the first treated using the method described above and the second comparison ring saturated with water for simple immersion. This is in order to extract any air present in the mesh of the two suture rings.

In practice, the test device was formed with a vacuum pump connected to a vacuum bell having an observation window. This circuit was subjected to the action of a Jofra LPCA hand-operated vacuum calibrator in order to bring the pressure to a level not less than −20 mbar. Two beakers full of a previously de-gassed aqueous solution were introduced into the bell. The two suture rings (one treated according to the invention, and the other as a comparison) described above were immersed in these beakers. The behavior was recorded by video recorder through the observation window in the bell.

Three successive tests were performed. In all three, no escape of residual air was detected in the suture rings treated according to the invention and, therefore, no residual air was present. On the other hand, the escape, and therefore the presence, of air was clearly detected in the untreated rings.

Device 10 shown in FIG. 1 corresponds to just one of the many possible embodiments of the invention and, the basic principle of the invention remaining the same, the arrangement described lends itself to many variations, some of which are particularly significant. For example, even without substantially modifying the structure of the device shown in FIG. 1, cup-like holding body 12 can be integrated into the structure of clamp 17, or pillar 30 that supports bag 23 can be integrated into the structure of clamp 17. In a complementary manner, vacuum bell 11 can itself be formed so as firmly to seal the vacuum without using an external structure such as clamp 17. Such an example of this is a container for keeping grocery products sealed, for example, of the type currently known as an albarello seal.

In addition, it is possible to envision the use of the container which holds the prosthesis as the vacuum bell. For example, with reference to FIG. 3, half-shell 1 can have a connector such as connector 16 (the use of the same reference numeral as utilised in FIG. 1 is intended to show this possible correspondence) with the possible modification of the mechanism for coupling two half-shells 1 and 2, for example, using a sealing ring such as an O-ring. This is so as to be able to utilise directly the casing defined by the half-shells 1 and 2 sealingly coupled together as a vacuum bell. To this end, connector 16 is configured so as to enable the connection to a source of sub-atmospheric pressure (for example, pump 27 via fluid line 26). At the same time, connector 16 is configured as a means for introducing into the casing formed from half-shells 1 and 2 the liquid intended to saturate the apertured structure of the prosthesis. That is, liquid would be drawn into the casing because of the sub-atmospheric pressure induced in the casing itself. This therefore means that the casing of the prosthesis container is directly connectable to a source of sub-atmospheric pressure (pump 27) and a source of liquid (bag 23) in order to effect the treatment described above without having to prepare vacuum bell 11 for this purpose. To this end, the container (in this case, the casing defined by half-shells 1 and 2) must have a structure that ensures the integrity of the prosthesis contained therein when the level of sub-atmospheric pressure (for example, −850 mbar) is reached.

Similarly, one or more arcuate slots, indicated 200, are usually present in the lower half-shell 2 of the container shown in FIG. 3. These slots are normally closed by one or more sheets, for example, of the material known as Tyvek™ already mentioned above, which is able to act as a sterile, fluid-permeable barrier. Naturally, when the prosthesis container is to be utilised as the vacuum bell, these slots must be closed, for example, with one or more elements (for example, self adhesive) acting as a seal or sealing plug, as schematically indicated 201 in FIG. 3.

In particular, where it is integrated with a container, connector 16 can be a different type and shape from the luer-type of connection referred to specifically in FIG. 3. It can, for example, utilise a different kind of luer connection (for example, a male connector in place of a female connector, or vice versa). Connector 16 could also be in communication with a liquid introduction means such as a perforable membrane which can be pierced with a needle, the axial lumen of which leads to valve 24. As is known, a luer connector also can be integral with a perforable membrane. That is, a luer-type connector and a perforable membrane could be used either to connect to the liquid source and/or to the vacuum source.

The choice of one of these arrangements, or alternative connection arrangements that are well known to one skilled in the art, is clearly correlated to the nature of the container utilised as the vacuum bell and/or the requirement of ensuring the necessary conditions of sterility of the connector before use.

An arrangement can also be proposed in which the vacuum bell (whether separate or constituted by the prosthesis container) includes a tank for the filling liquid, thus avoiding the necessity of having to use an external reservoir or container such as bag 23 and the connection line (indicated 25 in FIG. 1), and the associated elements.

It is equally clear that the reference to a cardiac valve prosthesis provided with a suture ring, as an apertured part, is purely by way of example. The arrangement according to the invention in fact lends itself to be utilised with any prosthesis including at least one part apertured in the terms referred to in the introduction to the present description. It can therefore be any kind of prosthesis (to give an example, a vascular prosthesis, including a prosthesis made from microporous material such as a vascular prostheses made from expanded polytetrafluoroethylene (PTFE)) which can be introduced directly into vacuum chamber 11 or located in this treatment chamber when the prosthesis itself is still in an associated sterile container, such as inner container 3 of FIG. 3, with the requirement of ensuring the accessibility of the apertured part of the prosthesis by the treatment liquid remaining, of course, the same.

It follows therefore that, the principle of the invention remaining the same, the details of construction and the embodiments can be widely varied with respect to that described and illustrated, without departing from the ambit of the present invention.

What is claimed is:

1. A method for the treatment of a cardiac valve prosthesis having an apertured structure, comprising:

placing a cardiac valve prosthesis having an apertured structure into a holding chamber;

producing sub-atmospheric pressure in the holding chamber;

introducing physiological saline into the holding chamber;

allowing the physiological saline to saturate the cardiac valve prosthesis; and removing the cardiac valve prosthesis from the holding chamber, to form a physiological saline-containing cardiac valve prosthesis suitable for implantation.

2. A method according to claim 1, wherein the sub-atmospheric pressure is selected so that after the introduction of the physiological saline into the holding chamber, the cardiac valve prosthesis is substantially free of air.

3. A method according to claim 1, wherein the step of producing sub-atmospheric pressure comprises connecting the holding chamber to a vacuum line; and the step of introducing physiological saline into the holding chamber comprises connecting the holding chamber to a liquid supply line, the liquid supply line being provided with a cut-off element.

4. A method according to claim 1, wherein the sub-atmospheric pressure of the holding chamber is approximately −850 mbar.

5. A method according to claim 3, wherein the holding chamber is connected to the vacuum line for less than about 60 seconds.

6. A method according to claim 1, wherein the liquid flows into the chamber for less than about 60 seconds.

* * * * *